(12) United States Patent
Li et al.

(10) Patent No.: US 10,603,497 B2
(45) Date of Patent: Mar. 31, 2020

(54) INVERTED E-ANTENNA FOR IMPLANTABLE MEDICAL DEVICES

(71) Applicant: PACESETTER, INC., Sylmar, CA (US)

(72) Inventors: Perry Li, Arcadia, CA (US); Wisit Lim, Santa Clarita, CA (US); Dino Bortolin, Camarillo, CA (US)

(73) Assignee: Pacesetter, Inc., Sylmar, CA (US)

(*) Notice: Subject to any disclaimer, the term of this patent is extended or adjusted under 35 U.S.C. 154(b) by 182 days.

(21) Appl. No.: 15/829,239

(22) Filed: Dec. 1, 2017

(65) Prior Publication Data

US 2019/0168005 A1   Jun. 6, 2019

(51) Int. Cl.
| | | |
|---|---|---|
| *H01Q 1/27* | (2006.01) | |
| *H01Q 1/36* | (2006.01) | |
| *A61N 1/372* | (2006.01) | |
| *A61N 1/375* | (2006.01) | |
| *A61B 7/00* | (2006.01) | |
| *A61B 5/00* | (2006.01) | |
| *A61B 5/024* | (2006.01) | |
| *A61B 5/021* | (2006.01) | |

(52) U.S. Cl.
CPC .......... *A61N 1/37229* (2013.01); *A61B 5/021* (2013.01); *A61B 5/024* (2013.01); *A61B 5/4809* (2013.01); *A61B 5/686* (2013.01); *A61B 7/00* (2013.01); *A61N 1/375* (2013.01); *H01Q 1/273* (2013.01); *A61B 5/0031* (2013.01); *A61B 7/003* (2013.01); *H01Q 1/36* (2013.01)

(58) Field of Classification Search
CPC .......... H01Q 1/22; H01Q 1/2291; H01Q 1/24; H01Q 1/241; H01Q 1/27; H01Q 1/273; H01Q 1/36; H01Q 9/26; H01Q 9/42; H01Q 9/46; A61N 1/37229
See application file for complete search history.

(56) References Cited

U.S. PATENT DOCUMENTS

| | | | |
|---|---|---|---|
| 2014/0002314 A1* | 1/2014 | Li et al. | .......... H01Q 1/36 343/718 |
| 2015/0255858 A1* | 9/2015 | Li et al. | ......... H01Q 1/273 343/718 |

* cited by examiner

*Primary Examiner* — Daniel Munoz
*Assistant Examiner* — Patrick R Holecek
(74) *Attorney, Agent, or Firm* — Dean D. Small; The Small Patent Law Group, LLC

(57) ABSTRACT

An implantable medical device and method are provided for implant within a patient. The device comprises a case. Radio frequency (RF) communication components are housed within the case. A header is mounted to an exterior surface of the case along an edge of the case. An antenna is coupled to the RF communication components. The antenna has an inverted E shape. The inverted E shaped antenna is within the header. The inverted E shaped antenna includes a conducting arm joined to first, second and third branches that are oriented within the header to extend toward the edge of the case underneath the header. The first branch of the antenna is conductively open and, no more than weakly coupled, with respect to the case. The second branch is located between the first and third branches. The second branch is configured to convey an RF signal feed. The third branch has a shunt to ground connection to the case. The case forms a ground plane for the antenna.

22 Claims, 7 Drawing Sheets

INVERTED E-ANTENNA FOR IMPLANTABLE MEDICAL DEVICES

BACKGROUND

Embodiments of the present embodiments described herein generally relate to implantable medical devices, and more particularly to antennas for use therein.

An implantable medical device ("IMD") is a medical device that is configured to be implanted within a patient anatomy and commonly employ one or more leads with electrodes that either receive or deliver voltage, current or other electromagnetic pulses (generally "energy") from or to an organ or tissue for diagnostic or therapeutic purposes. In general, IMDs include a battery, electronic circuitry, such as a pulse generator and/or a processor module, that are hermetically sealed within a metal housing (generally referred to as the "can"), and a microprocessor that is configured to handle radio frequency (RF) communication with an external device, as well as control patient therapy.

IMDs are programmed and monitored by an external programmer or external home-based patient care system. RF circuitry and an antenna are embedded within the housing of the IMD, such as the header or adjacent to the header, to allow data communication with the external device or base system. In the past, the IMD was configured to communicate bi-directionally with the external programmer or base system using the Medical Implant Communication Service ("MICS") specification. The MICS specification is defined under 47 C.F.R. 95.601-95.673 Subpart E (incorporated herein by reference) and ETSI EN 301 839-1 (incorporated herein by reference). The MICS protocol uses a frequency band between 402-405 MHz and a transmit power of approximately 25 microwatts. Problems have arisen in designing the antenna for use in the IMDs. In particular, there can be a loss of RF communication performance due to the reduction in size of the header and the housing (also called the "can" or "case") of the IMD. Further, attenuation is inherent to the system since the RF signal travels through the lossy human body.

Another problem is how to assemble an efficient RF antenna into a compact space such as an IMD header. It has been proposed to provide a loop or an inverted E-shaped configuration antenna mounted on the IMD. The antenna makes use of a capacitive plate at a tip in order to tune to a correct frequency of approximately 400 Mhz. Due to the frequency tuning, the capacitive plate allows a reduction in the electrical length of the antenna to enable the antenna to fit physically within the header of an IMD. While the proposed antenna works very well for the MICS frequency band, the proposed antenna is better suited for frequencies in the lower RF region (less than 1 GHz). With the introduction of Bluetooth Low Energy (BLE) communications in IMD, the operating frequency increases to 2.4 GHz which is a 6× increase from 400 MHz MICS communication.

SUMMARY

In accordance with embodiments herein, an implantable medical device is provided for implant within a patient. The device comprises a case. Radio frequency (RF) communication components are housed within the case. A header is mounted to an exterior surface of the case along an edge of the case. An antenna is coupled to the RF communication components. The antenna has an inverted E shape. The inverted E shaped antenna is within the header. The inverted E shaped antenna includes a conducting arm joined to first, second and third branches that are oriented within the header to extend toward the edge of the case underneath the header. The first branch of the antenna is conductively open and, no more than weakly coupled, with respect to the case. The second branch is located between the first and third branches. The second branch is configured to convey an RF signal feed. The third branch has a shunt to ground connection to the case. The case forms a ground plane for the antenna.

Optionally, the first branch may exhibit a capacitive component independent of, and not based on, coupling to the case. The first branch of the antenna may exhibit a capacitive component that forms a factor in defining a resonant frequency of the antenna. The capacitive component of the open branch that affects the resonant frequency is not due to coupling with the case. The second branch of the antenna may be coupled to the RF communication components within the case via a feedthrough of a feedthrough assembly. An inductance of the third branch may be set based on a length of the third branch. A resonant frequency of the antenna may be adjustable based on one or more of: relative lengths of the first, second and third branches; an inductance of the third branch; a location of the second branch relative to the third branch and a cross-sectional area of at least one of the first, second and third branches. The implantable medical device may be a cardiac rhythm management device. The RF components may be configured to utilize, as a wireless communication protocol, at least one of Bluetooth low energy, Bluetooth, or WiFi.

Optionally, a distal end of the first branch may be formed with a paddle shaped segment configured to provide a physical structure to hold the open branch at a desired position within the header. The paddle shaped segment may be oriented substantially perpendicular to a ground plane in order that no substantive capacitive relation is formed between the first branch and the case. The first branch may be formed integral with the conducting arm and may be bent in a curved or zig-zag shape. A length of the conducting arm may be at least 3 times longer than a length of the first branch. The conducting arm may be positioned proximate to, and extends along, an upper surface of the header. The first and third branches may be positioned within the header to extend along a loading face and a back end of the header, respectively. The first, second and third branches may be routed downward away from the conducting arm to extend toward a surface of the case.

In accordance with embodiments herein, a method of providing an antenna for use in an implantable medical device for implant within a patient is provided. The device comprising a case and radio frequency (RF) communication components housed within the case. The method provides an antenna having an inverted E shape. The inverted E shaped antenna includes a conducting arm joined to first, second and third branches that are oriented within the header to extend toward the edge of the case underneath the header. The second branch is located between the first and third branches. The method connects the second branch to the RF communications components to convey an RF signal feed and connects the third branch with a shunt to ground connection to the case. The case forms a ground plane for the antenna. The method maintains the first branch conductively open and, no more than weakly coupled, with respect to the case and tunes the antenna to a resonant frequency of at least 1 GHz.

Optionally, the method may further comprise tuning the antenna to a resonant frequency of 2.4 GHz. The tuning may further comprise tuning the antenna by adjusting one or more of: relative lengths of the first and second antenna sub-structures; a capacitance of the first antenna substructure; a location of the second antenna sub-structure relative to the first antenna sub-structure and a cross-sectional area of the at least one of the first, second and third branches, The first branch may exhibit a capacitive component independent of; and not based on, coupling to the case. The first branch of the antenna may exhibit a capacitive component that forms a factor in defining a resonant frequency of the antenna. The capacitive component of the open branch that affects the resonant frequency is not due to coupling with the case. The method may adjust resonant frequency of the antenna based on one or more of relative lengths of the first, second and third branches; an inductance of the third branch; a location of the second branch relative to the third branch and a cross-sectional area of at least one of the first, second and third branches. The method may comprise utilizing, as a wireless communication protocol, at least one of Bluetooth low energy, Bluetooth, or WiFi.

BRIEF DESCRIPTION OF THE DRAWINGS

These and other features, aspects, and advantages will be more fully understood when considered with respect to the following detailed description, the appended claims, and the accompanying drawings.

DETAILED DESCRIPTION

The description that follows sets forth one or more illustrative embodiments. It will be apparent that the teachings herein may be embodied in a wide variety of forms, some of which may appear to be quite different from those of the disclosed embodiments. Consequently, the specific structural and functional details disclosed herein are merely representative and do not limit the scope of the disclosure. For example, based on the teachings herein one skilled in the art should appreciate that the various structural and functional details disclosed herein may be incorporated in an embodiment independently of any other structural or functional details. Thus, an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

The terms "ambient coupling", "ambiently coupled", "weakly coupled", "weak coupling" and similar terms, are used interchangeably herein to mean that only weak capacitive coupling, is formed between the first or open branch of an antenna and any other metallic or electrically conductive components in the header. As an example, ambient or weak coupling means that the antenna exhibits an aggregate capacitance of 0.1-2.5 picofarads (pF), and more preferably an aggregate capacitance between 0.1 pF-1.5 pF, in connection with an operating frequency 1 GHz or greater. For the avoidance of doubt, the open branch may experience very limited aggregate capacitive coupling to the connectors, wires, pins and the like in the header of the IMD. While the open branch of the antenna exhibits a capacitive component that forms a factor in defining a resonant frequency of the antenna, the capacitive component of the open branch that affects the resonant frequency is primarily due to coupling between the open branch and components within the header. The capacitive component is independent of, and not based on, coupling to the case.

Figure 1A:
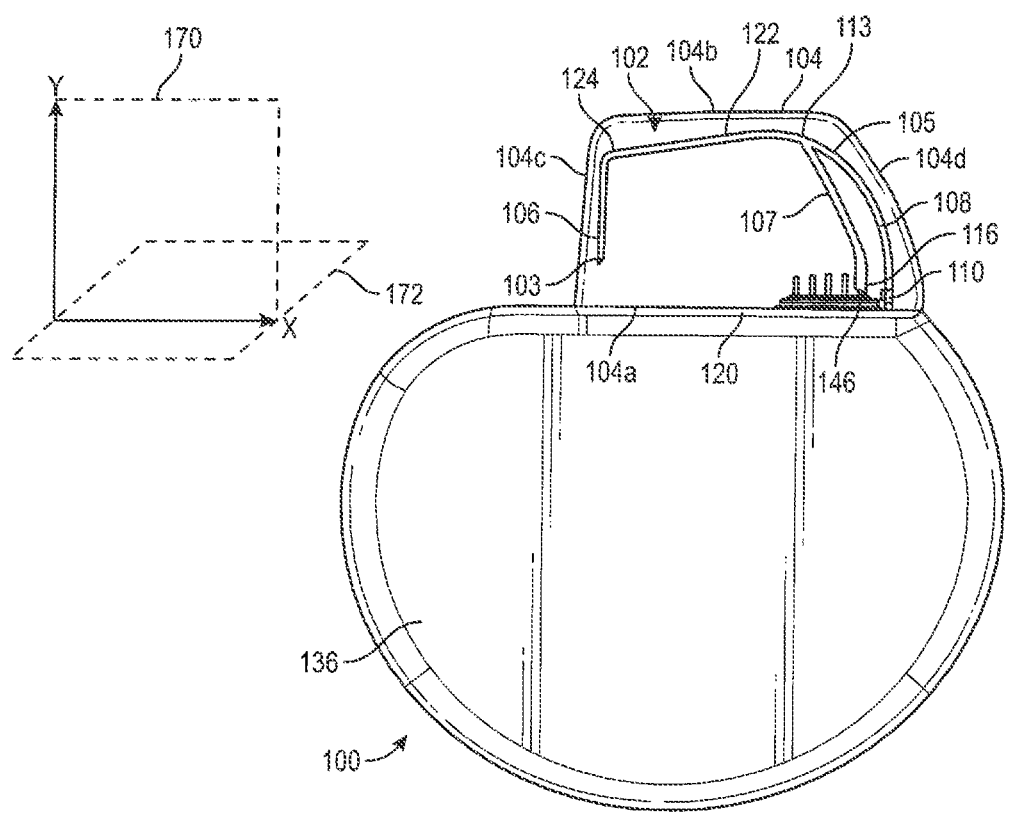
FIG. 1A illustrates an IMD having an antenna installed within a header mounted to an exterior surface of a case along an edge of the IMD in accordance with embodiments herein.

FIG. 1A illustrates an IMD 100 having an antenna 102 installed within a header 104 mounted to an exterior surface of a case 136 along an edge (e.g., only along a single edge, top surface 120) of the IMD 100. FIG. 1A illustrates the header 104 to be transparent; however, the header 104 may be opaque in various other embodiments. Although not shown in FIG. 1A, additional components mount within the header 104, such as components for connecting the IMD 100 to the proximal ends of pacing or sensing leads near the heart. The additional components may communicate to the internal components of the IMD (e.g., the electrode configuration switch) via the alternative feedthroughs 146 of the terminal.

The IMD includes a case 136 formed as a generally thin rectangular or oval body with flat opposed sides. The case 136 is elongated in the direction of the sides, which generally corresponds to a plane 170, also referred to as a case or antenna plane 170. The case 136 includes a top surface 120, to which a base of the header 104 is mounted. The interface between the top surface 120 of the case 136 and the base of the header 104 generally defines a transverse plane 172 that is perpendicular to the plane 170. For points of reference, the plane 170 may also be referred to as a vertical or antenna plane, while the transverse plane 172 may also be referred to as a horizontal or ground plane.

The antenna 102 may be an omnidirectional antenna that radiates and/or receives RF electromagnetic fields uniformly or equally in all horizontal directions (e.g., along or parallel to the transverse plane 172). It is understood that the antenna 102 also radiates and/or receives RF electromagnetic field in directions that are not parallel to the transverse plane 172. Thus, the antenna 102 may transmit or receive wireless communications equally without limiting the position of the IMD 100 within the patient with respect to the external device. The header 104 includes a base or lower surface 104a mounted to a top or upper surface 120 of the case 136. The top surface 120 of the case 136 aligns generally parallel to the transverse plane 172 and extends from a loading face 104c end to a back end 104d of the header 104 thereby providing a ground plane for the antenna 102. The upper surface 104b is located opposite to, and remote from, the lower surface 104a. The loading face 104c includes one or more openings therein that are configured to receive the terminals on a proximal end of one or more leads. The back end 104d is located opposite to and remote from the loading end 104c.

The antenna 102 is formed with an inverted E-shape that is oriented within and extending along the plane 170 of the case 136. The antenna 102 includes first, second and third branches 106, 108, and 107 protruding from a conducting arm 122 that provides a "backbone" or main body for the antenna 102. The conducting arm 122 may be formed from a horizontal piece of metal ribbon, while the first, second and third branches 106, 108 and 107 are oriented to extend generally perpendicular from the metal ribbon. By way of example, the conducting arm 122 and first, second and third branches 106, 108 and 107 may be stamped and formed from a common piece of metal, or alternatively machined from a common piece of metal. The conducting arm 122 is positioned at an uppermost point within the header 104, to extend along a top of the header 104 proximate to the upper surface 104b. The branches 106 and 108 are positioned within the header 104, to extend along the loading face 104c and back end 104d, respectively. The branches 106, 108 and 107 are routed downward, away from the conducting arm 122, to extend toward a surface of the case 136.

The second or middle branch 107 is also referred to as an RF signal feed branch 107. The RF signal feed branch 107 is positioned between the first branch 106 and third branch 108 and joins the conducting arm 122 at a node 113 along a central portion of the header 104. The RF signal feed branch 107 extends from the conducting arm 122 towards the case 136 along the common antenna plane 170. The RF signal feed branch 107 couples to the RF components (e.g., RF circuit) of the IMD 100 via an RF connector 116. The RF connector 116 couples to at least one of a set of feedthrough pins 146 extending from the case 136. On the other side of the feedthrough, in the interior of the case 136, the feedthrough pin 146 is connected to an RF transceiver and other RF circuitry. Optionally, the RF signal feed branch 107 may be coupled to the feedthrough pin 146 via welding. The RF signal feedthrough branch 107 serves as the feedthrough point where RF signals (e.g., BLE signals) may be sent between the RF transceiver and the antenna 102.

Optionally, the RF signal feed branch 107 may be mounted at a position closer to the loading face 104c or the backend 104d of the header 104 traversing along the conducting arm 122, as appropriate.

The third branch 108 may also be referred to as an inductive branch or inductive leg. The inductance of the third branch 108 is set based on a length, cross-section and other characteristics of the third branch. The inductive branch 108 includes a distal end connected to the case 136 at a connection 110. The case 136 serves as an electrical ground for the RF circuit within the IMD and thus, shorting the antenna 102 to the case 136 provides a large inductance to the antenna 102. The connection 110 is provided in various manners, such as by welding a distal end of the inductive branch 108 to an anchor structure attached to the case or welding the distal end of the inductive branch 108 to a ground/case feedthrough pin. The inductive branch 108 is positioned at the back end 104d of the header 104 and is formed integral with the conducting arm 122 at a smooth curve 105 to extend toward the case 136. The inductive branch 108 is connected at connection 110 to the conducting top surface 120 to provide a shunt to ground. A length of the inductive branch 108 may be adjusted during antenna design to vary the inductance of the antenna 102 to help achieve a desired impedance and/or resonant frequency of the antenna 102. Additionally or alternatively, a discrete inductor may be mounted to the inductive branch 108 (or elsewhere on the antenna 102) to provide additional impedance or to electrically lengthen the inverted E-shaped antenna (e.g., to increase the resonant frequency) if desired.

The first branch 106, also referred to as an open leg, is maintained in an unconnected state to provide an open circuit capacitance to the antenna 102. The open branch 106 includes a proximal end that is integrally joined to the conducting arm 122 at a bend 124 and extends towards the case 136 along the antenna plane 170. The open branch 106 includes a distal end 103 that may float or remain open, thereby affording a large amount of flexibility in how the open branch 106 is routed or otherwise implemented within the header 104. In the present example, the open branch 106 bends to extend toward the top surface 120 of the case 136 and is oriented to remain perpendicular to the conducting arm 122. As explained herein, the open branch 106 is configured to be ambiently coupled or weakly coupled to the case of the IMD. Optionally, the open branch 106 may extend in other directions. Optionally, the length, shape and routing of the open branch 106 may be varied in order to change an overall capacitance component that the open branch 106 contributes to the antenna 102. The length, shape and routing of the open branch 106 may be used to offset extra inductance or capacitance that is present due to a size and placement of the antenna 102.

The antenna 102 is tuned to a resonant frequency at or greater than 1 GHz. For example, in connection with embodiments that communicate using the BLE operating frequency, the antenna 102 is tuned to a resonant frequency of approximately 2.4 GHz. A resonant frequency of the antenna 102 is tuned/adjustable based on one or more of relative lengths of the first, second and third branches; an inductance of the third branch; a location of the second branch relative to the third branch and a cross-sectional area of at least one of the first, second and third branches. Additionally or alternatively, any of the four antenna segments, namely the conducting arm 122, open branch 106, inductive branch 108 or feed branch 107 may be lengthened or shortened, in order to achieve a desired balance for the capacitance versus inductance exhibited by the overall antenna 102. The position and length of the inductive branch 108 and open branch 106 may depend upon the form factor of the header 104 and select performance requirements (e.g., a signal return loss).

The antenna 102 is tuned to a predetermined resonant frequency to provide a signal performance exhibiting a lower return loss (e.g., no more than −5 dB) at the predetermined resonant frequency (e.g., 2.4 GHz) relative to alternative frequencies. By way of example, the resonant frequency of the antenna 102 may be tuned by adjusting relative dimensions of the conducting arm 122 and branches 106, 107 and 108. As a further example, the resonant frequency may be tuned by changing the material or metal used to construct the antenna 102, and by adjusting the cross sectional thickness, area, or shape of the branches 106, 107, and 108.

In accordance with embodiments herein, by providing an open branch, various antenna may be built that overcome challenges of operating a small antenna capable of fitting within a header of an IMD. The antenna are correctly sized to resonate at a chosen operating frequency such that the antenna have little or no net inductance or capacitance. Embodiments herein avoid "under sizing" an electrically small antenna which may otherwise generate unwanted capacitance or inductance at an operating frequency. By avoiding or substantially limiting unwanted capacitance or inductance at an antenna operating frequency, embodiments herein avoid unwanted effects in connection there with (e.g., reduced antenna gain, large antenna impedance mismatch and the like).

The invertedE-shaped antenna described herein provide an open branch (capacitive end) and an inductive branch (inductive end) with a feed branch there between in order to balance the two ends. By changing the length and structure of the open and inductive branches, the capacitance/inductance of the antenna may be varied. Embodiments herein provide an electrically small antenna capable of operating at a BLE frequency and/or any other high frequency over 1 GHz, with tuning capabilities that are allowed by altering the lengths of the open and inductive branches to provide a manner to eliminate or substantially reduce excessive capacitance and inductance. The antenna described herein are easily tunable with a high degree of flexibility, thereby rendering the antenna suitable for assembly in headers with different sizes. For example, when an antenna is intended to be placed in a relatively smaller header, the conducting arm may need to be similarly shortened. Consequently, the feed branch, open branch and/or inductive branch may be independently tuned (e.g., changed in length) to compensate for the changes in the length of the conducting arm, thereby affording options for resizing of the antenna for ease in manufacturability.

Figure 1B:
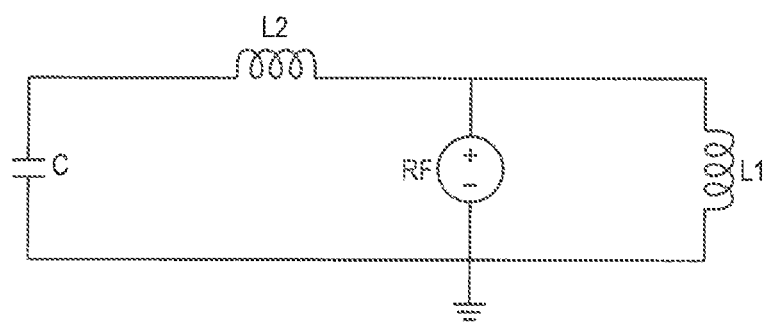
FIG. 1B illustrates an example LC model for the antenna formed in accordance with embodiments herein.

FIG. 1B illustrates a simplified example LC model for the antenna formed in accordance with embodiments herein. The LC model includes a signal source RF, a first inductor L1, a second inductor L2, and a capacitor C. The capacitor C and second inductor L2 are connected in series, with the series combination of C and L2 connected in parallel with the signal source RF. The signal source RF is also connected in parallel with the first inductor L1. By way of example, the signal source RF represents the feed branch 107, the first inductor L1 represents the inductive branch 108, and the series LC combination of the capacitor C and second inductor L2 represents the open branch 106. The resonance frequency of the LC model can be found when the imaginary term on the left side of the RF source (L2 and C) matches the imaginary term on the right side of the RF Source (L1). The values for the capacitor C and inductors L1, L2 may be tuned by adjusting the length of the open branch 106 and inductive branch 108.

Figure 2:
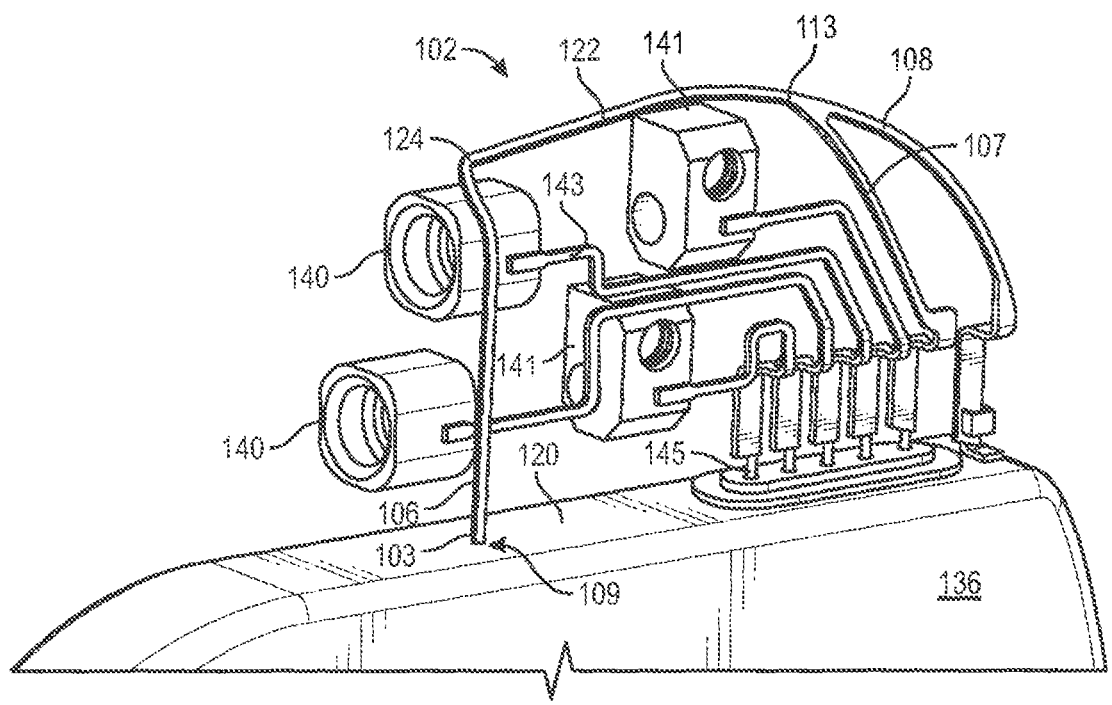
FIG. 2 illustrates a side perspective view of the antenna of FIG. 1A in accordance with an embodiment herein.

FIG. 2 illustrates a side perspective view of the antenna of FIG. 1A in accordance with an embodiment herein. FIG. 2 also illustrates an example of some additional components that may be present within certain types of headers. The antenna 102 is positioned adjacent lead terminal receptacles 140 and 141. The lead terminal receptacles 140 and 141 are configured to receive conductive terminals on proximal ends of one or more leads. The lead terminal receptacles 140, 141 join conductive lines 143 and corresponding feedthrough pins 145 to form a conductive path between corresponding electrodes provided on the lead and the sensing/stimulation circuitry within the IMD. The open branch 106 of the antenna 102 extends along a side of the lead terminal receptacles 140, with the lead terminal receptacles 141 located in an open area between the open branch 106 and the feed branch 107. As shown in FIG. 2, the distal end 103 of the open branch 106 is spaced apart from the top surface 120 of the case 136 by a gap 109. The distal end 103 of the open branch 106 has a weak capacitive coupling to the case 136. The first or open branch 106 exhibits a capacitive component that is independent of, and not based on, coupling to the case 136. For example, the distal end 103 of the open branch 106 is spaced the predetermined gap 109 away from the top surface 120 of the case 136 such that that no substantive capacitive relation is formed between the first or open branch 106 and the case 136. While the open branch 106 exhibits a capacitive component that forms a factor in defining a resonant frequency of the antenna, the capacitive component of the open branch 106 that affects the resonant frequency is not due to any form of coupling with the case 136.

In accordance with embodiments of FIGS. 1 and 2, the open branch 106 includes a substantially constant width and thickness along a length thereof. Optionally, the width and/or thickness may vary along portions of the open branch 106 such as illustrated in FIG. 3.

Figure 3A:
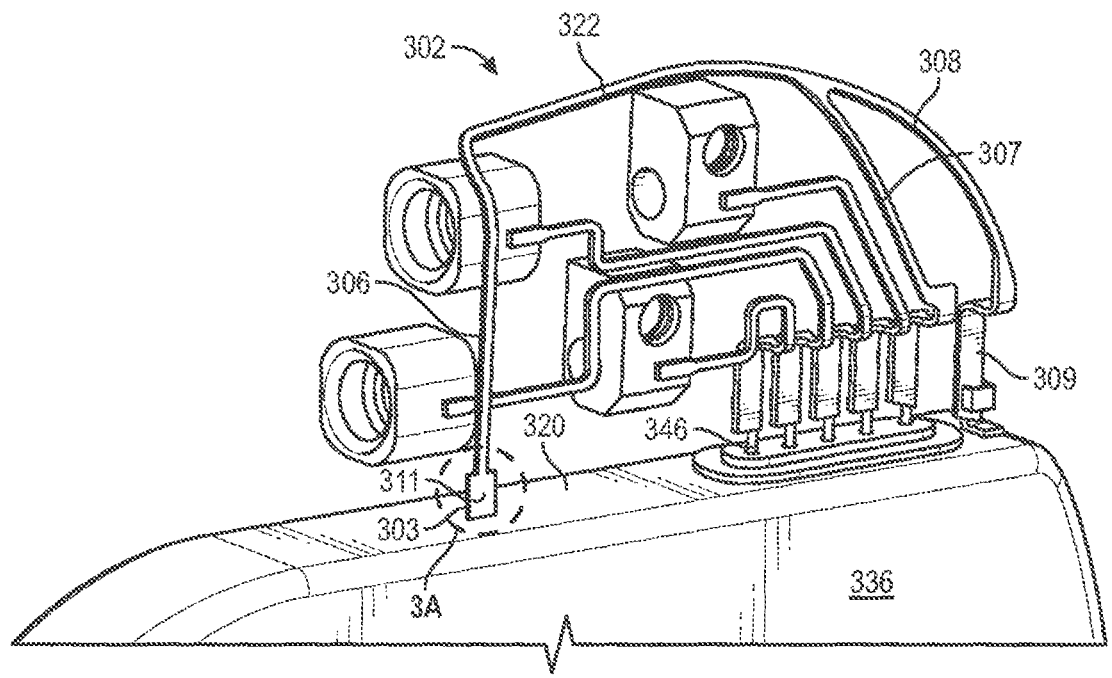
FIGS. 3A and 3B illustrate a side perspective view of an antenna formed in accordance with an alternative embodiment.

FIG. 3A illustrates a side perspective view of an antenna formed in accordance with an alternative embodiment. The antenna 302 includes a feed branch 307 joined to a conducting arm 322 at a position between an open branch 306 and an inductive branch 308. A distal end of the feed branch 307 connects to a feedthrough pin 346 and a distal end of the inductive branch 308 includes a contact pad 309 that is joined to a case 336 of an IMD. The antenna 302 of FIG. 3A differs from the antenna 102 of FIG. 2 at least in connection with the open branch 306. A distal end 303 of the open branch 306 is formed with a paddle shaped segment 311 having cross-sectional dimensions that differ from the cross-section of the open branch 306. The paddle shaped segment 311 provides a physical structure to hold the open branch 306 at a desired position within the header.

Figure 3B:
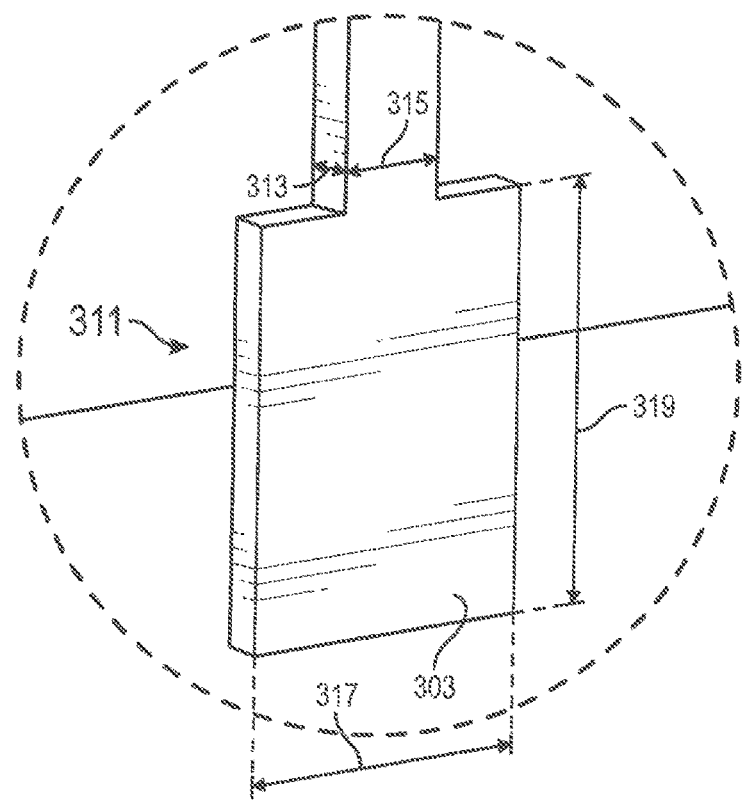

As shown in FIG. 3B, the open branch 306 has a thickness 313 and a width 315 that may be similar or slightly vary from one another. The paddle shaped segment 311 has a length 319 and a width 317 and is oriented to extend parallel the antenna or case plane (e.g., plane 170 in FIG. 1). The width 317 of the paddle shaped segment 311 is substantially greater than the width 315 (e.g., three times greater, five times greater) of the intermediate portion of the open branch 306. The paddle shaped segment 311 may have a thickness that is the same as the thickness 313. The length 319 and/or width 317 of the paddle shaped segment 311 may be adjusted to vary the capacitance exhibited by the open branch 306.

The paddle shaped segment 311 is oriented substantially perpendicular to the ground plane 172 in order that no substantive capacitive relation is formed between the first or open branch 306 and the case 336. In addition to the orientation the paddle shaped segment 311, the distal end 303 of the paddle shaped segment 311 is spaced at least a predetermined gap away from the upper surface 320 of the case 336 such that that no substantive capacitive relation is formed between the first or open branch 306 and the case 336. While the open branch 306 exhibits a capacitive component that forms a factor in defining a resonant frequency of the antenna, the capacitive component exhibited by the open branch 306 that affects the resonant frequency is not due to coupling with the case 336. The first or open branch 306 exhibits a capacitive component that is independent of, and not based on, coupling to the case.

Figure 4:
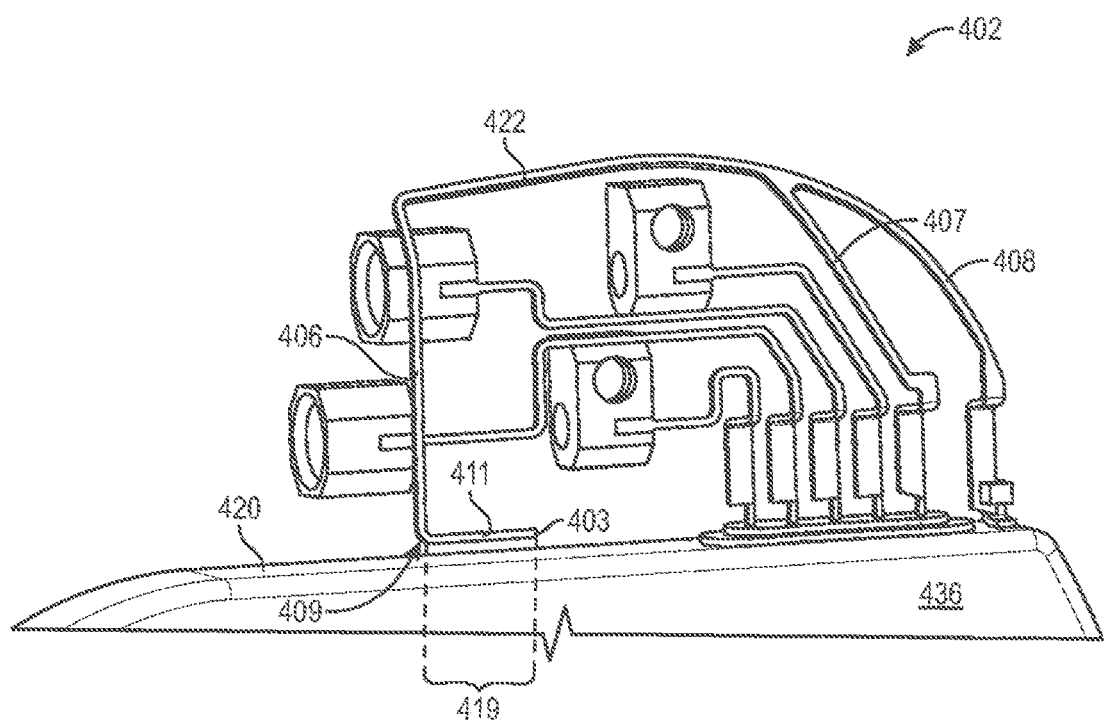
FIG. 4 illustrates a side perspective view of an antenna formed in accordance with an alternative embodiment.

FIG. 4 illustrates a side perspective view of an antenna formed in accordance with an alternative embodiment. The antenna 402 includes a feed branch 407 joined to a conducting arm 422 at a position between an open branch 406 and an inductive branch 408. A distal end of the feed branch 407 connects to a feedthrough pin and a distal end of the inductive branch 408 includes a contact pad that is joined to a case 436 of an IMD. The antenna 402 of FIG. 4 differs from the antenna 102 of FIG. 2 at least in connection with the open branch 406. A distal end 403 of the open branch 306 is formed with a foot segment 411 that is bent to extend in a direction substantially parallel to the conducting arm 422, the transverse plane 172 and the upper surface 420 of the case 436. The foot segment 411 has a length 419 that may be varied in connection with tuning the antenna 422. The foot segment 411 has a width and thickness substantially similar to the width and thickness of a remaining portion of the open branch 406. The foot segment 411 is spaced apart from the upper surface 420 by a gap 409 that varies in connection with tuning the antenna 402.

Figure 5A:
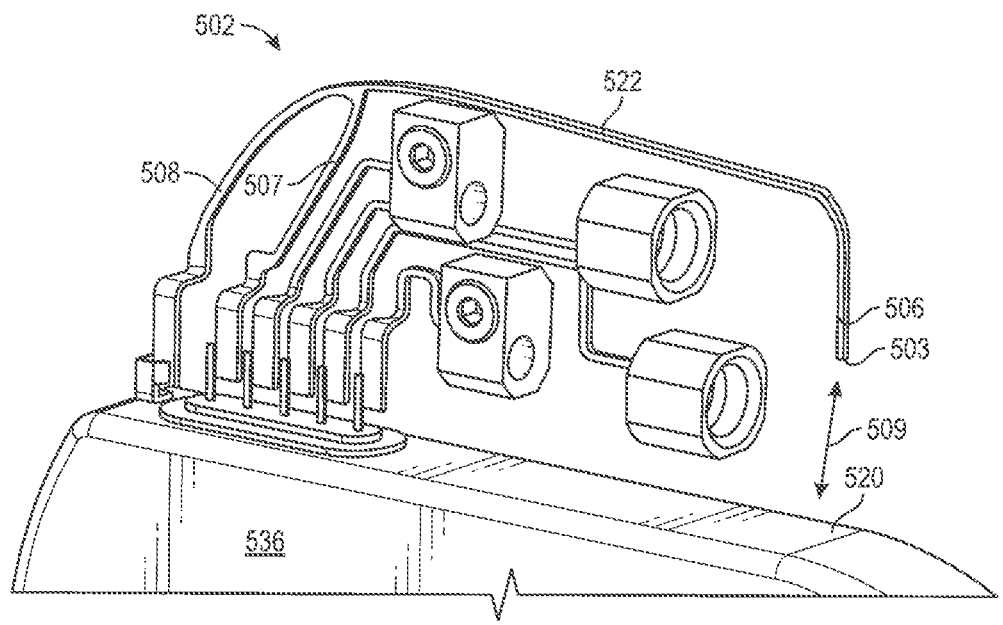
FIG. 5A illustrates a side perspective view of an antenna formed in accordance with an alternative embodiment.

FIG. 5A illustrates a side perspective view of an antenna formed in accordance with an alternative embodiment. The antenna 502 includes a feed branch 507 joined to a conducting arm 522 at a position between an open branch 506 and an inductive branch 508. A distal end of the feed branch 507 connects to a feedthrough pin and a distal end of the inductive branch 508 includes a contact pad that joins a case 536 of an IMD. The antenna 502 of FIG. 5A differs from the antenna 102 of FIG. 2 at least in connection with a length of the open branch 506. The open branch 506 is formed with a substantially shorter overall length as compared to a length of the open branches 106, 306 and 406 such that a distal end 503 of the open branch 506 spaced a substantially greater distance from an upper surface 520 of the case 536 (as denoted by gap 509). The length of the open branch 506 (e.g., as measured from the bend 124 to the distal end 103) may be shortened relative to a length of the conducting arm 522 (e.g., as measured from the node 113 to the bend 124). For example, the conducting arm 522 may be at least 3 times longer or at least 4 times longer than the open branch 506.

Figure 5B:
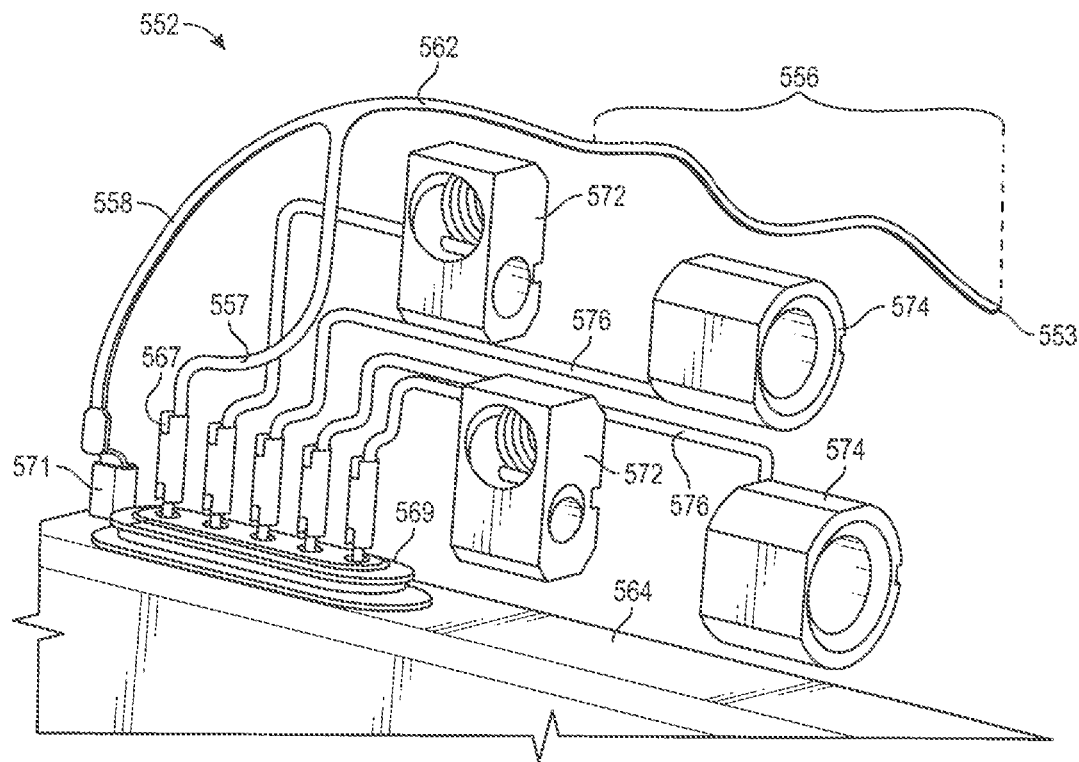
FIG. 5B illustrates an exemplary inverted E antenna in detail along with other components that installed within a device header for coupling to pacing, sensing and/or shocking leads in accordance with embodiments herein.

In the example of FIG. 1A, the first, second and third branches 106, 107 and 108 are shown to be generally straight. Optionally, the branches 106, 108, 107 may be curved in different directions, such as a curved or zig-zag pattern. FIG. 5B illustrates an exemplary inverted E antenna 552 in detail along with other components that installed within a device header for coupling to pacing, sensing and/or shocking leads. The antenna 552 includes a conducting arm 562 along with first, second and third branches 556, 557 and 558. The open branch 556 is formed integral with the conducting arm 562 and is bent in a curved or zig-zag shape to the distal end 553. The RF signal feed branch 557 is connected from a middle portion of the conducting arm 562 to internal RF components of the device via an RF lead connection 567 mounted to a feedthrough assembly 569. The inductive branch 558 extends from conducting arm 562 and connects to conducting surface 564 via an RF case connector 571 to provide a shunt to ground. Additionally, FIG. 5B shows components 572 and 574 for connecting proximal ends of the leads to internal components of the IMD via various connection lines 576 to feedthrough assembly 569. In one example, components 572 are tip connectors for connecting to conductors within the leads that couple to tip electrodes at the distal ends of the leads. Components 574 are ring connectors for connecting to conductors of the leads that couple to ring electrodes at the distal ends of the leads.

For example, in accordance with embodiments herein, as a height of the header decreases, the branches of the antenna grow shorter. To compensate for the shortening of the branches, the conducting arm may be made longer, thereby resulting in a desired antenna resonant frequency and radiation performance. Thus, the examples of FIGS. 1A-5B illustrative examples of different shapes and sizes for the branches and conducting arm that may be utilized to fit various header form factors.

Figure 6:
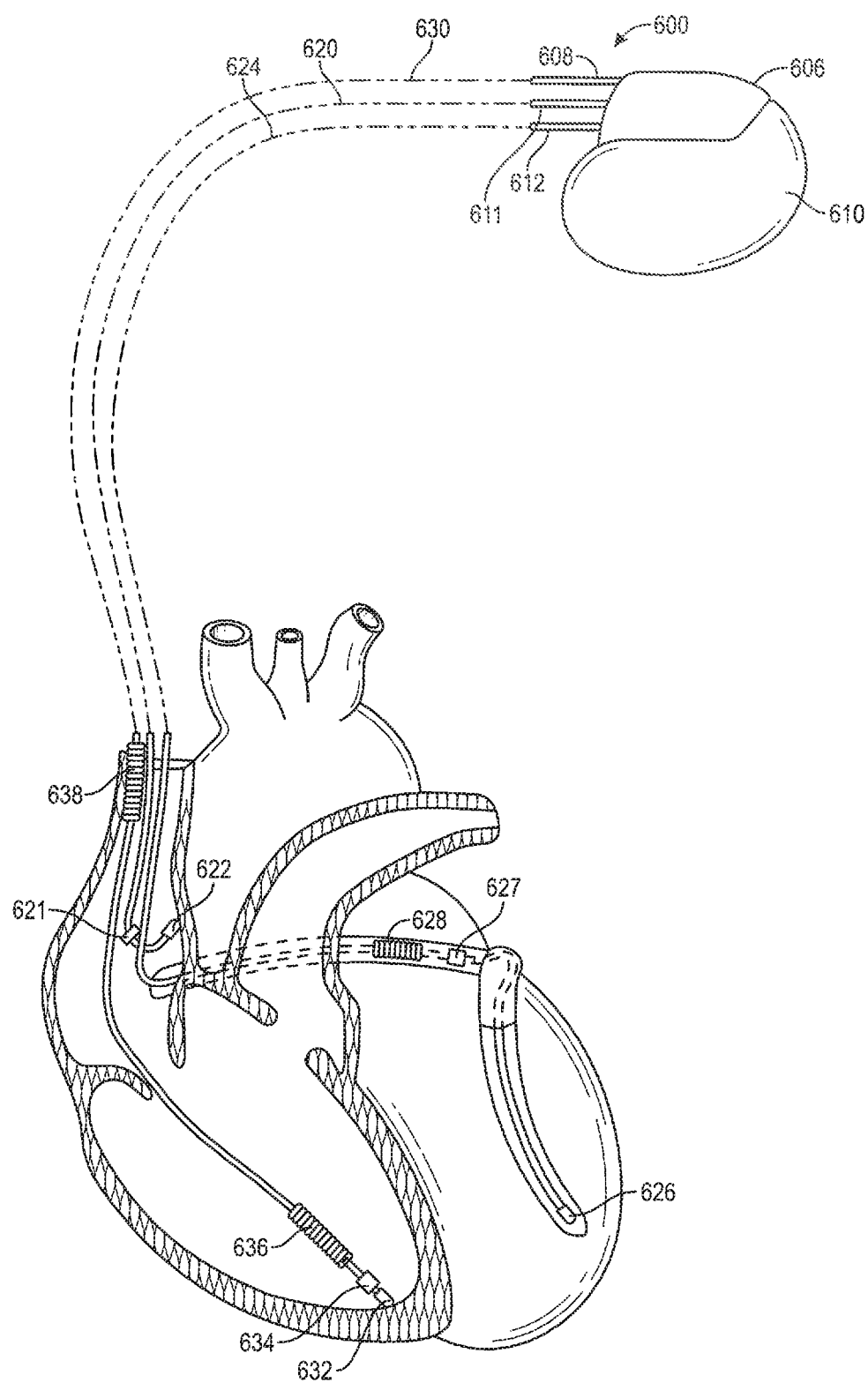
FIG. 6 illustrates an IMD a heart in a patient and implemented in accordance with one embodiment.

FIG. 6 illustrates an IMD 600 a heart in a patient and implemented in accordance with one embodiment. The IMD 600 may be a cardiac pacemaker, an implantable cardioverter-defibrillator (ICD), a defibrillator, an ICD coupled with a pacemaker, and the like, implemented in accordance with one embodiment of the present invention. The IMD 600 may be a dual-chamber stimulation device capable of treating both fast and slow arrhythmias with stimulation therapy, including cardioversion, defibrillation, and pacing stimulation, as well as capable of detecting heart failure, evaluating its severity, tracking the progression thereof, and controlling the delivery of therapy and warnings in response thereto. The IMD 600 may be controlled to sense atrial and ventricular waveforms of interest, discriminate between two or more ventricular waveforms of interest, deliver stimulus pulses or shocks, and inhibit application of a stimulation pulse to a heart based on the discrimination between the waveforms of interest and the like. An exemplary structure for the IMD 600 is discussed and illustrated below in connection with FIG. 7.

The IMD 600 includes a housing 610 joined to a header assembly 606 that holds receptacle connectors 608, 611, 612 connected to a right ventricular lead 630, a right atrial lead 620, and a coronary sinus lead 624, respectively. The leads 630, 620, and 624 measure cardiac signals of the heart. The right atrial lead 620 includes an atrial tip electrode 622 and an atrial ring electrode 621. The coronary sinus lead 624 includes a left ventricular tip electrode 626, a left atrial ring electrode 627, and a left atrial coil electrode 628. The right ventricular lead 630 has an RV tip electrode 632, an RV ring electrode 634, an RV coil electrode 636, and an SVC coil electrode 638. The leads 630, 620, and 624 detect IEGM signals that form an electrical activity indicator of myocardial function over multiple cardiac cycles.

Figure 7:
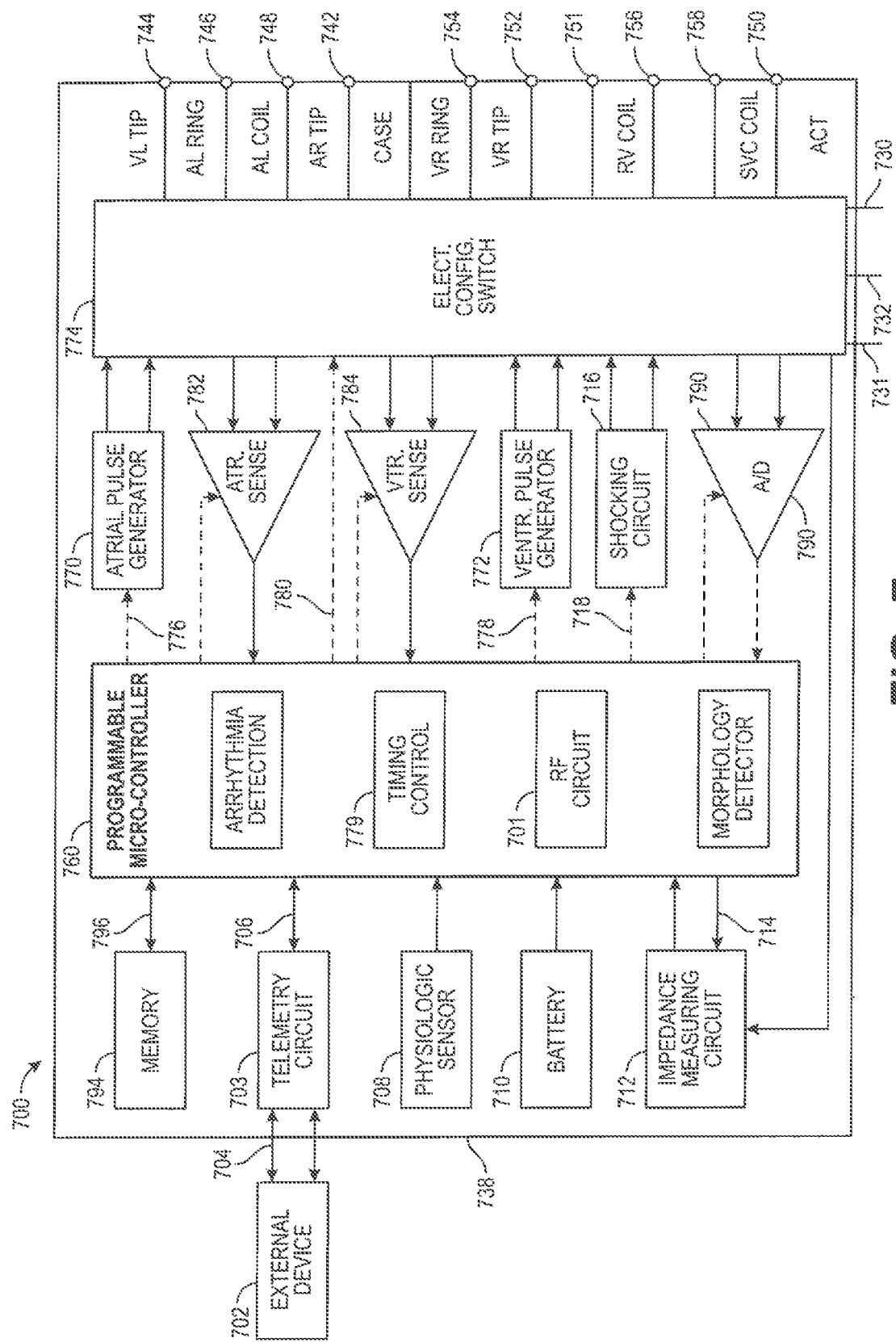
FIG. 7 illustrates a block diagram of exemplary internal components of an IMD in accordance with embodiments herein.

FIG. 7 illustrates a block diagram of exemplary internal components of an IMD 700. The systems described herein can include or represent hardware and associated instructions (e.g., software stored on a tangible and non-transitory computer readable storage medium, such as a computer hard drive, ROM, RAM, or the like) that perform the operations described herein. The hardware may include electronic circuits that include and/or are connected to one or more logic-based devices, such as microprocessors, processors, controllers, or the like. These devices may be off-the-shelf devices that perform the operations described herein from the instructions described above. Additionally or alternatively, one or more of these devices may be hard-wired with logic circuits to perform these operations.

The IMD 700 is for illustration purposes only, and it is understood that the circuitry could be duplicated, eliminated or disabled in any desired combination to provide a device capable of treating the appropriate chamber(s) with cardioversion, defibrillation and/or pacing stimulation as well as providing for apnea detection and therapy. A case 738 for IMD 700, shown schematically in FIG. 6, is often referred to as the "can", "housing" or "case electrode" and may be programmably selected to act as the return electrode for all "unipolar" modes. The casing 738 may further be used as a return electrode alone or in combination with one or more of the coil electrodes for shocking purposes. The casing 738 further may include a connector (not shown) having a plurality of terminals, 742, 746, 748, 752, 754, 756 and 758 (shown schematically and, for convenience, the names of the electrodes to which they are connected are shown next to the terminals). A right atrial tip terminal (AR TIP) 742 may be adapted for connection to the atrial tip electrode and a right atrial ring terminal may be adapted for connection to right atrial ring electrode. A left ventricular tip terminal (VL TIP) 744, a left atrial ring terminal (AL RING) 746, and a left atrial shocking terminal (AL COIL) 748 may be adapted for connection to the left ventricular ring electrode, and a left atrial tip electrode and a left atrial coil electrode respectively. A right ventricular tip terminal (VR TIP) 752, a right ventricular ring terminal (VR RING) 754, a right ventricular shocking terminal (RV COIL) 756, and an SVC shocking terminal (SVC COIL) 758 may be adapted for connection to the right ventricular tip electrode, right ventricular ring electrode, an RV coil electrode, and an SVC coil electrode, respectively.

An acoustic terminal (ACT) 750 may be adapted to be connected to an external acoustic sensor or an internal acoustic sensor, depending upon which (if any) acoustic sensors are used. Terminal 751 may be adapted to be connected to a blood sensor to collect measurements associated with glucose levels, natriuretic peptide levels, or catecholamine levels.

The IMD 700 may include a programmable microcontroller 760 which controls operation of the IMD 700. The microcontroller 760 (also referred to herein as a processor module or unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 760 includes the ability to process or monitor input signals (data) as controlled by program code stored in memory. The details of the design and operation of the microcontroller 760 are not critical to the invention. Rather, any suitable microcontroller 760 may be used that carries out the functions described herein. Among other things, the microcontroller 760 receives, processes, and manages storage of digitized cardiac data sets from the various sensors and electrodes. For example, the cardiac data sets may include IEGM data, pressure data, heart sound data, and the like.

The IMD 700 may include an atrial pulse generator 770 and a ventricular/impedance pulse generator 772 to generate pacing stimulation pulses for delivery by the right atrial lead 730, the right ventricular lead 731, and/or the coronary sinus lead 732 via an electrode configuration switch 774. It is understood that in order to provide stimulation therapy in each of the four chambers of the heart, the atrial and ventricular pulse generators, 770 and 772, may include dedicated, independent pulse generators, multiplexed pulse generators or shared pulse generators. The pulse generators, 770 and 772, are controlled by the microcontroller 760 via appropriate control signals, 776 and 778, respectively, to trigger or inhibit the stimulation pulses.

The IMD 700 may include a neuro stimulation pulse generator circuit (not illustrated) to generate stimulation pulses for a brain or spinal cord nervous system. The stimulation pulses are delivered by a plurality of electrodes through a neuro output lead. The neuro stimulation pulse generator circuit may be controlled by the microcontroller 760 via appropriate control signals to trigger or generate the stimulation pulses.

The microcontroller 760 may further include timing control circuitry 779 used to control the timing of stimulation pulses (e.g., pacing rate, atria-ventricular (AV) delay, atrial inter-conduction (A-A) delay, or ventricular inter-conduction (V-V) delay, etc.), as well as, to keep track of the timing of refractory periods, blanking intervals, noise detection windows, evoked response windows, alert intervals, marker channel timing, and the like. Switch 774 includes a plurality of switches for connecting the desired electrodes to the appropriate I/O circuits, thereby providing complete electrode programmability. Accordingly, the switch 774, in response to a control signal 780 from the microcontroller 760, determines the polarity of the stimulation pulses (e.g., unipolar, bipolar, etc.) by selectively closing the appropriate combination of switches (not shown) as is known in the art.

Atrial sensing circuit 782 and ventricular sensing circuit 784 may also be selectively coupled to the right atrial lead 730, coronary sinus lead 732, and the right ventricular lead 731, through the switch 774 for detecting the presence of cardiac activity in each of the four chambers of the heart. Accordingly, the atrial (ATR SENSE) and ventricular (VTR SENSE) sensing circuits, 782 and 784, may include dedicated sense amplifiers, multiplexed amplifiers or shared amplifiers. The outputs of the atrial and ventricular sensing circuits, 782 and 784, are connected to the microcontroller 760 which, in turn, are able to trigger or inhibit the atrial and ventricular pulse generators, 770 and 772, respectively, in a demand fashion in response to the absence or presence of cardiac activity in the appropriate chambers of the heart.

Cardiac signals are also applied to the inputs of an analog-to-digital (A/D) data acquisition system 790. The data acquisition system 790 is configured to acquire IEGM signals, convert the raw analog data into a digital IEGM signal, and store the digital IEGM signals in memory 794 for later processing and/or radio frequency (RF) transmission to an external device 702. The data acquisition system 790 may be coupled to the right atrial lead 730, the coronary sinus lead 732, and the right ventricular lead 731 through the switch 774 to sample cardiac signals across any combination of desired electrodes. The data acquisition system 790 may also be coupled, through switch 774, to one or more of the acoustic sensors. The data acquisition system 790 acquires, performs A/D conversion, produces and saves the digital pressure data, and/or acoustic data.

The microcontroller 760 may control the acoustic sensor and/or a physiologic sensor to collect heart sounds during one or more cardiac cycles. The heart sounds include sounds representative of a degree of blood flow turbulence. The acoustic sensor and/or physiologic sensor collects the heart sounds that include S1, S2 and linking segments. The S1 segment is associated with initial systole activity. The S2 segment is associated with initial diastole activity. The linking segment is associated with at least a portion of heart activity occurring between the S1 and S2 segments during a systolic interval between the initial systole and diastole activity. The microcontroller 760 changes a value for at least one of the pacing parameters between the cardiac cycles. The microcontroller 760 implements one or more processes described herein to determine values for one or more pacing parameters that yield a desired level of hemodynamic performance.

The microcontroller 760 is coupled to memory 794 by a suitable data/address bus 796, wherein the programmable operating parameters used by the microcontroller 760 are stored and modified, as required, in order to customize the operation of IMD 700 to suit the needs of a particular patient. The memory 794 also stores data sets (raw data, summary data, histograms, etc.), such as the IEGM data, heart sound data, pressure data, Sv02 data and the like for a desired period of time (e.g., 1 hour, 24 hours, 1 month). The memory 794 may store instructions to direct the microcontroller 760 to analyze the cardiac signals and heart sounds identify characteristics of interest and derive values for predetermined statistical parameters. The IEGM, pressure, and heart sound data stored in memory 794 may be selectively stored at certain time intervals, such as 1 minutes to 1 hour periodically or surrounding a particular type of arrhythmia of other irregularity in the heart cycle. For example, the memory 794 may store data for multiple non-consecutive 10 minute intervals.

The IMD 700 may also include an accelerometer or other physiologic sensor 708, commonly referred to as a "rate-responsive" sensor used to record the activity level of the patient or adjust pacing stimulation rate according to the exercise state of the patient. Optionally, the physiological sensor 708 may further be used to detect changes in cardiac output, changes in the physiological condition of the heart, or changes in activity (e.g., detecting sleep and wake states) and movement positions of the patient. While shown as being included within IMD 700, it is to be understood that the physiologic sensor 708 may also be external to the IMD 700, yet still be implanted within or carried by the patient. A common type of rate responsive sensor is an activity sensor incorporating an accelerometer or a piezoelectric crystal, which is mounted within the casing 738 of the IMD 700.

The physiologic sensor 708 may be used as the acoustic sensor that is configured to detect the heart sounds. For example, the physiologic sensor 708 may be an accelerometer that is operated to detect acoustic waves produced by blood turbulence and vibration of the cardiac structures within the heart (e.g., valve movement, contraction and relaxation of chamber walls and the like). When the physiologic sensor 708 operates as the acoustic sensor, it may supplement or replace entirely acoustic sensors. Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient and, in particular, is capable of detecting arousal from sleep or other movement.

The IMD 700 includes a battery 710, which provides operating power to all of the circuits shown. The IMD 700 is shown as having impedance measuring circuit 712 which is enabled by the microcontroller 760 via a control signal 714. Herein, impedance is primarily detected for use in evaluating ventricular end diastolic volume (EDV) but is also used to track respiration cycles. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 712 is advantageously coupled to the switch 774 so that impedance at any desired electrode may be obtained.

The IMD 700 may also be operated as an implantable cardioverter/defibrillator (ICD) device, which detects the occurrence of an arrhythmia and automatically applies an appropriate electrical shock therapy to the heart aimed at terminating the detected arrhythmunia. To this end, the microcontroller 760 may further control a shocking circuit 716 by way of a control signal 718. The shocking circuit 716 may generate shocking pulses of low (e.g., up to 0.5 joules), moderate (e.g., 0.5-10 joules), or high energy (e.g., Z11 to 70 joules), as controlled by the microcontroller 760. Such shocking pulses are applied to the patient's heart through shocking electrodes. It is noted that the shock therapy circuitry is optional and may not be implemented in the IMD 700.

The pacing and other operating parameters of the IMD 700 may be non-invasively programmed into the memory 794 through a telemetry circuit 703 in telemetric communication 704 with the external device 702, such as a programmer, trans-telephonic transceiver, or a diagnostic system analyzer. The telemetry circuit 703 is activated by the microcontroller 760 by a control signal 706. The telemetry circuit 703 allows intra-cardiac electrograms, pressure data, acoustic data, Sv02 data, and status information relating to the operation of the IMD 700 (as contained in the microcontroller 760 or memory 794) to be sent to the external device 702 through an established communication link 704.

Depending upon the implementation, the microcontroller 760 may use an RF circuit 701. The RF circuit 701 includes RF communication components, such as a monolithic microwave integrated circuit (MMIC), coupled to an antenna (not specifically shown in FIG. 7). The RF circuit 701 allows the IMD 700 to facilitate telemetry using a wireless communication protocol such as Bluetooth low energy, Bluetooth, WiFi, Medical Implant Communication Service ("MICS"), WiFi, or the like. Wireless protocol firmware is stored in memory 794, and is accessed by the microcontroller 760 via the data bus 796. The protocol firmware provides the wireless protocol syntax for the microcontroller 760 to assemble data packets, establish communication links, and partition data received from the external device 702 through the antenna coupled to the RF circuit 701. The RF circuit 701 may support one or multiple wireless communication protocols that use varying operational frequencies.

Figure 8:
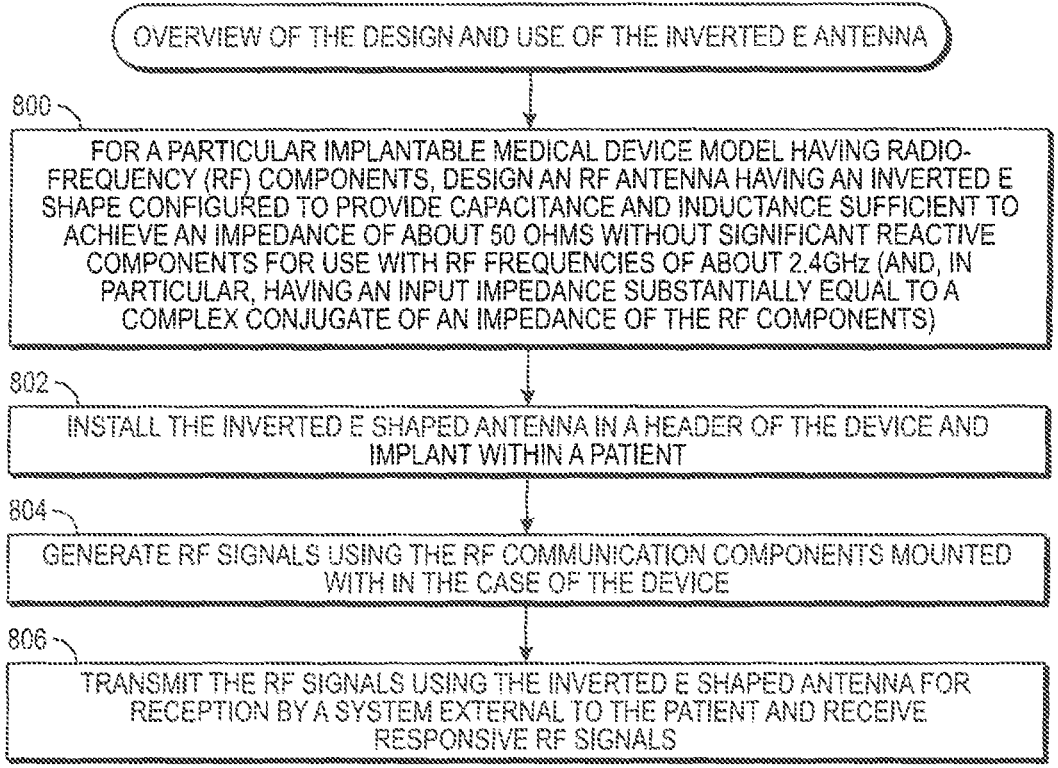
FIG. 8 illustrates a flowchart of a method for providing an antenna for use in an IMD for implant within a patient in accordance with embodiments herein.

FIG. 8 illustrates a flowchart of a method for providing a antenna for use in an IMD for implant within a patient. The method may be implemented as a software algorithm, package, or system that directs one or more hardware circuits or circuitry to perform the actions described herein. For example, the operations of the method may represent actions to be performed by one or more circuits that include or are connected with processors, microprocessors, controllers, microcontrollers, Application Specific Integrated Circuits (ASICs), Field-Programmable Gate Arrays (FPGAs), or other logic-based devices that operate using instructions stored on a tangible and non-transitory computer readable medium (e.g., a computer hard drive, ROM, RAM, EEPROM, flash drive, or the like), such as software, and/or that operate based on instructions that are hardwired into the logic thereof.

At least one technical effect of at least one portion of the method described herein includes i) providing an antenna, ii) tuning the antenna to different first and second resonant frequencies, respectively, having a desired return loss at a select resonant frequency, and iii) configuring the antenna to be coupled to the RF communication components in the case of the device.

FIG. 8 broadly summarizes a procedure for designing and using an inverted E antenna. Briefly, at step 800, for a particular implantable medical device model having RF components, an RF antenna having an inverted E shape is designed and configured to provide capacitance and inductance sufficient to achieve an impedance of, in one example, about 50 ohms without significant reactive components for use with RF frequencies of about 2.4 GHz (and, in particular, having an input impedance substantially equal to a complex conjugate of an impedance of the RF components.) In other examples, different values might be used to achieve a different impedance. At step 802, the inverted E shaped antenna is installed in a header of the device and implanted within a patient. At step 804, RF signals are generated using RF communication components mounted within the case of the device and, at step 806, the RF signals are transmitted using the inverted E shaped antenna for reception by a system external to the patient. Signals generated by the external system may also be received by the antenna and routed to the internal RF components of the implanted device for use in controlling the operation of the device. The broad summary of FIG. 8 does not, of course, set forth all steps that may be needed. In particular, approval by the U.S. Food and Drug Administration (FDA) or other regulatory authorities may be required before implant of the device within a patient.

Although primarily described with respect to examples wherein the implanted device is a CRMD, other implantable medical devices may be equipped to exploit the techniques described herein. Where appropriate, the antenna described herein may be used in conjunction with other antenna design features. Also, it should be understood that any "optimal" antenna parameters or dimensions described herein are not necessarily absolutely optimal in a mathematical sense. What constitutes "optimal" depends on the criteria used for judging the resulting performance. The antenna parameters identified or selected using techniques described herein represent, at least, a "preferred" set of parameters. Designers may choose to adjust or alter the parameters at their discretion during device design.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose several embodiments of the inventive subject matter and also to enable a person of ordinary skill in the art to practice the embodiments of the inventive subject matter, including making and using any devices or systems and performing any incorporated methods. The patentable scope of the inventive subject matter is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The foregoing description of certain embodiments of the inventive subject matter will be better understood when read in conjunction with the appended drawings. To the extent that the Figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the inventive subject matter are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

The components and functions described herein may be connected or coupled in many different ways. The manner in which this is done may depend, in part, on whether and how the components are separated from the other components. In some embodiments some of the connections or couplings represented by the lead lines in the drawings may be in an integrated circuit, on a circuit board or implemented as discrete wires or in other ways.

What is claimed is:

1. An implantable medical device for implant within a patient, the device comprising:
   a case;
   radio frequency (RF) communication components housed within the case;
   a header mounted to an exterior surface of the case along an edge of the case; and
   an antenna coupled to the RE communication components, the antenna having an inverted E shape, wherein the inverted E shaped antenna is within the header;
   wherein the inverted E shaped antenna includes a conducting arm joined to first, second and third branches that are oriented within the header to extend toward the edge of the case underneath the header,
   the first branch of the antenna being conductively open, and having an open distal end extending toward the edge of the case such that the first branch is no more than weakly coupled, with respect to the case,
   the second branch located between the first and third branches, the second, branch configured to convey an RF signal feed, and
   the third branch having a shunt to ground connection to the case, the case forming a ground plane for the antenna.

2. The device of claim 1 wherein the first branch exhibits a capacitive component independent of, and not based on, coupling to the case.

3. The device of claim 1 wherein the first branch of the antenna exhibits a capacitive component that forms a factor in defining a resonant frequency of the antenna, and wherein the capacitive component of the first branch that affects the resonant frequency is not due to coupling with the case.

4. The device of claim 1 wherein the second branch of the antenna is coupled to the RF communication components within the case via a feedthrough of a feedthrough assembly.

5. The device of claim 1 wherein the third branch represents an inductive branch tuned to have a select inductance.

6. The device of claim 1 wherein a resonant frequency of the antenna is adjustable based on one or more of; i) relative lengths of the first, second and third branches, ii) an inductance of the third branch, iii) a location of the second branch relative to the third branch and iv) a cross-sectional area of at least one of the first, second and third branches.

7. The device of claim 1 wherein the open branch is tuned to have a capacitance of 0.1 pF 2.5 pF.

8. The device of claim 1 wherein the RF components are configured to utilize, as a wireless communication protocol, at least one of Bluetooth low energy, Bluetooth, or WiFi.

9. The device of claim 1, wherein the distal end of the first branch is formed with a paddle shaped segment configured to provide a physical structure to hold the open branch at a desired position within the header, the paddle shaped segment oriented substantially perpendicular to a ground plane in order that no substantive capacitive relation is formed between the first branch and the case.

10. The device of claim 1, wherein the first branch is formed integral with the conducting arm and is bent in a curved or zig-zag shape.

11. The device of claim 1, wherein a length of the conducting arm is at least 3 times longer than a length of the first branch.

12. The device of claim 1, wherein the conducting arm is positioned proximate to, and extends along, an upper surface of the header, and where the first and third branches are positioned within the header to extend along a loading face and a back end of the header, respectively.

13. The device of claim 1, wherein the first, second and third branches are routed downward away from the conducting arm to extend toward a surface of the case.

14. The device of claim 1 wherein the open end of the first branch is spaced apart from the edge of the case by a gap to maintain the first branch no more than weakly coupled, with respect to the case.

15. A method of providing an antenna for use in an implantable medical device for implant within a patient, the device comprising a case, a header and radio frequency (RE) communication components housed within the case, the method comprising:
providing an antenna having an inverted E shape, the inverted E shaped antenna includes a conducting arm joined to first, second and third branches that are oriented within the header to extend toward the edge of the case underneath the header, the second branch located between the first and third branches;
connecting the second branch to the RF communications components to convey an RF signal feed;
connecting the third branch with a shunt to ground connection to the case, the case forming a ground plane for the antenna;
maintaining the first branch conductively open with an open distal end of the first branch extending toward the edge of the case such that the first branch is no more than weakly coupled, with respect to the case; and
tuning the antenna to a resonant frequency of at least 1 GHz.

16. The method of claim 15, further comprising tuning the antenna to a resonant frequency of 2.4 GHz.

17. The method of claim 15, wherein the tuning further comprises tuning the antenna by adjusting one or more of: i) relative lengths of the first and second antenna sub-structures, ii) a capacitance of the first antenna substructure, iii) a location of the second antenna sub-structure relative to the first antenna sub-structure and iv) a cross-sectional area of the at least one of the first, second and third branches.

18. The method of claim 15 wherein the first branch of the antenna exhibits a capacitive component that forms a factor in defining a resonant frequency of the antenna, and wherein the capacitive component of the open branch that affects the resonant frequency is not due to coupling with the case.

19. The method of claim 15 further comprising adjusting a resonant frequency of the antenna based on one or more of: i) relative lengths of the first, second and third branches, ii) an inductance of the third branch, iii) a location of the second branch relative to the third branch and iv) a cross-sectional area of at least one of the first, second and third branches.

20. The method of claim 15 further comprising utilizing, as a wireless communication protocol, at least one of Bluetooth low energy, Bluetooth, or WiFi.

21. The method of claim 15 further comprising spacing the open distal end of the first branch apart from the edge of the case by a gap to maintain the first branch no more than weakly coupled, with respect to the case.

22. A method of providing an antenna for use in an implantable medical device for implant within a patient, the device comprising a case, a header and radio frequency (RE) communication components housed within the case, the method comprising:
providing an antenna having an inverted E shape, the inverted E shaped antenna includes a conducting arm joined to first, second and third branches that are oriented within the header to extend toward the edge of the case underneath the header, the second branch located between the first and third branches;
connecting the second branch to the RF communications components to convey an RE signal feed;
connecting the third branch with a shunt to ground connection to the case, the case forming a ground plane for the antenna;
maintaining the first branch conductively open and, no more than weakly coupled, with respect to the case, wherein the first branch exhibits a capacitive component independent of, and not based on, coupling to the case; and
tuning the antenna to a resonant frequency of at least 1 GHz.

* * * * *